United States Patent
Ohsumi et al.

(10) Patent No.: US 7,078,590 B2
(45) Date of Patent: Jul. 18, 2006

(54) METHOD FOR PROVIDING A PROPERTY OF STRESS-RESISTANCE

(75) Inventors: Chieko Ohsumi, Kanagawa (JP); Teruaki Taji, Ibaraki (JP); Kazuo Shinozaki, Ibaraki (JP)

(73) Assignees: Ajinomoto Co., Inc., Tokyo (JP); Riken, Wako (JP)

(*) Notice: Subject to any disclaimer, the term of this patent is extended or adjusted under 35 U.S.C. 154(b) by 183 days.

(21) Appl. No.: 09/810,186

(22) Filed: Mar. 19, 2001

(65) Prior Publication Data

US 2003/0074696 A1  Apr. 17, 2003

(30) Foreign Application Priority Data

Mar. 14, 2001  (JP) ............................. 2001-072668

(51) Int. Cl.
*C12N 15/82*  (2006.01)

(52) U.S. Cl. ..................................... 800/289
(58) Field of Classification Search ............ 435/320.1, 435/419, 468; 800/289, 298, 284
See application file for complete search history.

(56) References Cited

FOREIGN PATENT DOCUMENTS

| EP | 0 849 359 A2 | * | 6/1998 |
|----|--------------|---|--------|
| EP | 0 994 186 A1 | * | 4/2000 |
| JP | 0 849 359 A2 | * | 6/1998 |
| JP | 11123080 A   | * | 5/1999 |
| JP | 411123080 A  | * | 5/1999 |
| JP | 0 994 186 A1 | * | 4/2000 |

OTHER PUBLICATIONS

Bachmann et al., Metabolism of the Raffinose Family Oligosaccharides in Leaves of Ajuga reptans L.1, 1994, Plant Physiol. vol. 105, pp. 1335-1345.*
Geneseq Accession No. AAX61239, soybean raffinose synthase encoding cDNA, Jul. 29, 1999.*
U.S. Appl. No. 09/810,186, filed Mar. 19, 2001, Ohsumi, et al.
U.S. Appl. No. 10/778,054, filed Feb. 17, 2004, Taji, et al.

* cited by examiner

*Primary Examiner*—Cynthia Collins
(74) *Attorney, Agent, or Firm*—Oblon, Spivak, McClelland, Maier & Neustadt, P.C.

(57) ABSTRACT

The present invention enables production of a plant resistant to environmental stresses including drought stress. The invention increases stress resistance to a plant by increasing raffinose content in the plant.

20 Claims, 3 Drawing Sheets

SEQUENCE LISTING

<160> NUMBER OF SEQ ID NOS: 4

<210> SEQ ID NO 1
<211> LENGTH: 750
<212> TYPE: PRT
<213> ORGANISM: Glycine max

<400> SEQUENCE: 1

```
Met Thr Val Thr Pro Lys Ile Ser Val Asn Asp Gly Lys Leu Val Val
1               5                   10                  15

His Gly Lys Thr Ile Leu Thr Gly Val Pro Asp Asn Val Val Leu Thr
            20                  25                  30

Pro Gly Ser Gly Arg Gly Leu Val Thr Gly Ala Phe Val Gly Ala Thr
        35                  40                  45

Ala Ser His Ser Lys Ser Leu His Val Phe Pro Met Gly Val Leu Glu
    50                  55                  60

Gly Leu Arg Phe Met Cys Cys Phe Arg Phe Lys Leu Trp Trp Met Thr
65                  70                  75                  80

Gln Arg Met Gly Thr Cys Gly Arg Asp Val Pro Leu Glu Thr Gln Phe
                85                  90                  95

Met Leu Ile Glu Ser Lys Glu Ser Glu Thr Asp Gly Glu Asn Ser Pro
            100                 105                 110

Ile Ile Tyr Thr Val Leu Leu Pro Leu Leu Glu Gly Gln Phe Arg Ala
        115                 120                 125

Val Leu Gln Gly Asn Asp Lys Asn Glu Ile Glu Ile Cys Leu Glu Ser
    130                 135                 140

Gly Asp Asn Ala Val Glu Thr Asp Gln Gly Leu His Met Val Tyr Met
145                 150                 155                 160

His Ala Gly Thr Asn Pro Phe Glu Val Ile Asn Gln Ala Val Lys Ala
                165                 170                 175

Val Glu Lys His Met Gln Thr Phe Leu His Arg Glu Lys Lys Arg Leu
            180                 185                 190

Pro Ser Cys Leu Asp Trp Phe Gly Trp Cys Thr Trp Asp Ala Phe Tyr
        195                 200                 205

Thr Asp Val Thr Ala Glu Gly Val Glu Glu Gly Leu Lys Ser Leu Ser
    210                 215                 220

Gln Gly Gly Thr Pro Pro Arg Phe Leu Ile Ile Asp Asp Gly Trp Gln
225                 230                 235                 240

Gln Ile Glu Asn Lys Ala Lys Asp Ala Thr Glu Cys Leu Val Gln Glu
                245                 250                 255

Gly Ala Gln Phe Ala Thr Arg Leu Thr Gly Ile Lys Glu Asn Thr Lys
            260                 265                 270

Phe Gln Lys Lys Leu Gln Asn Asn Glu Gln Met Ser Gly Leu Lys His
        275                 280                 285

Leu Val His Gly Ala Lys Gln His His Asn Val Lys Asn Val Tyr Val
    290                 295                 300

Trp His Ala Leu Ala Gly Tyr Trp Gly Val Lys Pro Ala Ala Thr
305                 310                 315                 320
```

-continued

```
Gly Met Glu His Tyr Asp Thr Ala Leu Ala Tyr Pro Val Gln Ser Pro
            325                 330                 335

Gly Val Leu Gly Asn Gln Pro Asp Ile Val Met Asp Ser Leu Ala Val
            340                 345                 350

His Gly Leu Gly Leu Val His Pro Lys Lys Val Phe Asn Phe Tyr Asn
            355                 360                 365

Glu Leu His Ala Tyr Leu Ala Ser Cys Gly Val Asp Gly Val Lys Val
370                 375                 380

Asp Val Gln Asn Ile Ile Glu Thr Leu Gly Ala Gly His Gly Gly Arg
385                 390                 395                 400

Val Ser Leu Thr Arg Ser Tyr His His Ala Leu Glu Ala Ser Ile Ala
                405                 410                 415

Ser Asn Phe Thr Asp Asn Gly Cys Ile Ala Cys Met Cys His Asn Thr
                420                 425                 430

Asp Gly Leu Tyr Ser Ala Lys Gln Thr Ala Ile Val Arg Ala Ser Asp
                435                 440                 445

Asp Phe Tyr Pro Arg Asp Pro Ala Ser His Thr Ile His Ile Ser Ser
450                 455                 460

Val Ala Tyr Asn Ser Leu Phe Leu Gly Glu Phe Met Gln Pro Asp Trp
465                 470                 475                 480

Asp Met Phe His Ser Leu His Pro Ala Ala Asp Tyr His Ala Ala Ala
                485                 490                 495

Arg Ala Ile Gly Gly Cys Pro Ile Tyr Val Ser Asp Lys Pro Gly Asn
                500                 505                 510

His Asn Phe Asp Leu Leu Lys Lys Leu Val Leu Pro Asp Gly Ser Val
                515                 520                 525

Leu Arg Ala Gln Leu Pro Gly Arg Pro Thr Arg Asp Ser Leu Phe Val
            530                 535                 540

Asp Pro Ala Arg Asp Arg Thr Ser Leu Leu Lys Ile Trp Asn Leu Asn
545                 550                 555                 560

Lys Cys Ser Gly Val Val Gly Val Phe Asn Cys Gln Gly Ala Gly Trp
                565                 570                 575

Cys Lys Ile Glu Lys Lys Thr Arg Ile His Asp Thr Ser Pro Gly Thr
                580                 585                 590

Leu Thr Ala Ser Val Cys Ala Ser Asp Val Asp Leu Ile Thr Gln Val
            595                 600                 605

Ala Gly Ala Glu Trp Leu Gly Asp Thr Ile Val Tyr Ala Tyr Arg Ser
    610                 615                 620

Gly Glu Val Ile Arg Leu Pro Lys Gly Val Ser Ile Pro Val Thr Leu
625                 630                 635                 640

Lys Val Leu Glu Phe Glu Leu Phe His Phe Cys Pro Ile Gln Glu Ile
                645                 650                 655

Ala Pro Ser Ile Ser Phe Ala Ala Ile Gly Leu Leu Asp Met Phe Asn
                660                 665                 670

Thr Gly Gly Ala Val Glu Gln Val Glu Ile His Asn Arg Ala Ala Thr
    675                 680                 685

Lys Thr Ile Ala Leu Ser Val Arg Gly Arg Gly Arg Phe Gly Val Tyr
    690                 695                 700

Ser Ser Gln Arg Pro Leu Lys Cys Val Val Gly Gly Ala Glu Thr Asp
705                 710                 715                 720

Phe Asn Tyr Asp Ser Glu Thr Gly Leu Thr Thr Phe Ser Ile Pro Val
                725                 730                 735

Ser Pro Glu Glu Met Tyr Arg Trp Ser Ile Glu Ile Gln Val
```

<210> SEQ ID NO 2
<211> LENGTH: 2780
<212> TYPE: DNA
<213> ORGANISM: Glycine max

<400> SEQUENCE: 2

| | | | | | |
|---|---|---|---|---|---|
| tcttccattg | gaggaccatt | tcctcctgga | atagaaatac | taccacactt | ttctttttc | 60 |
| acttctctaa | gttgctaagt | taattgctcc | ttcattttt | cactcttcgt | tctcgcgtac | 120 |
| ccgtgtcacg | gtaactcgtg | gtgaagtgtt | cgaaaatgac | tgtcacacct | aagatctcag | 180 |
| ttaacgatgg | gaaacttgtt | gtccatggta | agaccattct | gactggagtg | ccagacaacg | 240 |
| ttgtgctgac | tccaggttct | ggaagggggtc | ttgtgactgg | tgcttttgtt | ggtgccacag | 300 |
| cttcacacag | caaaagtctc | catgtgtttc | caatgggtgt | tttagagggg | ctccggttca | 360 |
| tgtgttgttt | ccggttcaag | ttatggtgga | tgactcagag | aatgggaact | tgtgggaggg | 420 |
| atgttcctct | ggagactcaa | ttcatgctta | ttgagagcaa | agagagtgaa | actgatgggg | 480 |
| agaattctcc | aatcatctac | actgtcttgc | ttcctctcct | cgaaggtcaa | ttccgagctg | 540 |
| ttcttcaagg | caatgacaag | aacgagatag | agatttgcct | cgagagtggg | gataatgcag | 600 |
| ttgagactga | ccaaggcctt | cacatggttt | acatgcatgc | tgggaccaat | ccctttgaag | 660 |
| tcatcaatca | agctgtcaag | gctgtggaaa | acacatgca | aacttttctt | catcgtgaga | 720 |
| agaaaaggtt | gccatcttgt | cttgactggt | ttggatggtg | cacatgggat | gctttctata | 780 |
| ctgatgtcac | agctgagggt | gttgaggaag | gcctgaaaag | tctatcacag | ggaggtacac | 840 |
| ctccacgatt | cctcatcata | gatgatggtt | ggcaacagat | tgaaaataaa | gcaaaggatg | 900 |
| ctactgaatg | tttggtacaa | gaaggagcac | agtttgctac | taggttgact | ggtattaaag | 960 |
| agaatactaa | atttcaaaag | aaattacaga | acaatgagca | gatgtcaggt | ctgaagcatc | 1020 |
| tagtacatgg | agcaaagcag | catcacaatg | tgaaaaatgt | atatgtatgg | catgcactag | 1080 |
| ctggttattg | gggtggagtg | aagccagcag | caaccggcat | ggaacattat | gacactgcct | 1140 |
| tggcatatcc | agtgcagtca | ccaggcgtgc | taggaaaacca | accagacatt | gtcatggaca | 1200 |
| gcttggctgt | acatggcctt | ggcctagtgc | acccaaagaa | ggttttcaat | ttctacaacg | 1260 |
| agctccatgc | ttacttagct | tcttgtggag | tagatggagt | gaaggttgat | gtgcagaaca | 1320 |
| ttattgagac | ccttggtgcg | ggacatggtg | gccgagtgtc | acttactcgc | agctatcatc | 1380 |
| acgcgcttga | ggcttccatt | gctagcaatt | ttactgataa | cggatgcatt | gcgtgtatgt | 1440 |
| gtcacaacac | tgatggactt | tatagtgcta | agcagactgc | tattgtgaga | gcttctgatg | 1500 |
| atttttaccc | tcgtgatcct | gcttcccata | ccatccatat | ttcttctgtt | gcatacaact | 1560 |
| cactattcct | tggagaattc | atgcaacctg | actgggacat | gtttcatagt | ttacacccag | 1620 |
| cagcagatta | tcatgctgca | gctcgtgcaa | ttggtggatg | tcctatttat | gttagtgaca | 1680 |
| agccaggcaa | tcacaatttt | gatcttctta | agaagctggt | tctcccggat | ggttcggttc | 1740 |
| tccgtgctca | gttacctggc | aggccaactc | gtgattctct | atttgtggat | ccagccagag | 1800 |
| ataggactag | cttgctcaaa | atatggaacc | tgaacaaatg | ctctggagtt | gttggtgtat | 1860 |
| ttaactgcca | aggtgctgga | tggtgcaaga | tagagaagaa | aacccgcatc | catgatacat | 1920 |
| ctcctggtac | actcaccgcc | tctgtctgcg | cctctgatgt | tgacctcatc | acacaagtag | 1980 |
| caggtgctga | atggcttgga | gatacaattg | tttatgctta | cagatcaggt | gaggtgattc | 2040 |
| ggctaccaaa | agggggtttca | attccagtga | cactaaaagt | tctggagttt | gagcttttcc | 2100 |

```
                                                    -continued acttctgtcc aatccaagaa atagctccaa gtatatcatt tgcagcaata gggctactgg    2160
atatgttcaa cactggagga gcagtggagc aggttgagat tcataaccga gcagcaacga    2220
aaacaatagc tcttagtgta aggggaagag gcagatttgg agtttactcc tcccagagac    2280
cactgaagtg tgtggtaggt ggcgctgaaa ccgacttcaa ctatgactca gagaccgggt    2340
tgacaacctt ctccattcca gtttctccag aggagatgta cagatggtca atagagatcc    2400
aagtttgagt ccttttttaag acttggtgtt tgatgcattg ttgtatcagg agaagggttt    2460
tgttgtaatt aagcattgag ggaattgttg gagtcaggca gagagagagg ggggaggttt    2520
gttgtaagac acctagtatt agtatcatgt agtggagaaa aagggttgtt gatcctaata    2580
gctagacaag gcatgttgta gtagtcatgg ggtggggaag tccttttgtt gtagcatgta    2640
atttggttta gacttgtagt atgtcatcaa ttagatggat aaagagagaa tattgttatc    2700
tacccgagga tgtaacaatg tttgtttctc tgaataaaaa gttcacatct gtcttttgga    2760
ataataaaaa aaaaaaaaaa                                                2780

<210> SEQ ID NO 3
<211> LENGTH: 20
<212> TYPE: DNA
<213> ORGANISM: Artificial Sequence
<220> FEATURE:
<223> OTHER INFORMATION: Synthetic DNA

<400> SEQUENCE: 3
tttccggttc aagttatggt                                                 20

<210> SEQ ID NO 4
<211> LENGTH: 20
<212> TYPE: DNA
<213> ORGANISM: Artificial Sequence
<220> FEATURE:
<223> OTHER INFORMATION: Synthetic DNA

<400> SEQUENCE: 4
caatgcatcc gttatcagta                                                 20
```

METHOD FOR PROVIDING A PROPERTY OF STRESS-RESISTANCE

FIELD OF THE INVENTION

The present invention relates to a method for increasing stress-resistance to a plant. That is, the method can impart a plant with stress-resistance including good drought resistance and/or resistance to high salt concentration.

BACK GROUND OF THE INVENTION

The importance of agricultural use of the arid zone, which occupies approximately one third of the land on the earth, is increasingly recognized as a measure against predicted serious food scarcity. This problem should be addressed as soon as possible. Now the proportion of dry and semi-dry soil inappropriate for agriculture is increasing year after year due to saline accumulation, and drying or heat caused by, for example, excessive irrigation water (Manabu Sekiya, et al., Chemical Regulation in Plant Vol. 25, No. 2, 149–162, 1990). One of the solutions to this problem is a method in which resistance mechanisms against these environmental stresses are elucidated and a plant resistant to these stresses is produced.

Plants are immobile. Thus they must be tough enough to endure their environmental changes in order to keep differentiating and growing. Therefore, it is thought that plants have acquired through the course of evolution a response mechanism to respond promptly and adapt to environmental changes. Of the environmental factors surrounding plants, drought and saline accumulation are important factors concerning life or death of terrestrial plants. These factors largely affect plant growth. Plant growth is inhibited by drought stress. That is, it causes decreased turgor pressure and affects various physiological pathways (Shinozaki and Yamaguchi-Shinozaki, Plant Physiol. 115: 327–334, 1997).

In plants, it has been shown that various response mechanisms act against these stresses at an individual level, tissue level, and cellular level, and in addition through molecular biological research at a gene expression level. In other words, in various plants, a response mechanism at a gene expression level, including the presence of many stress-inducible genes whose mRNA amount increases upon drying and treatment with salt, has been elucidated. Plants are thought to acquire resistance from any one of the products of the stress-inducible gene group.

Abscisic acid (ABA), one of a plant's hormones, is deeply involved in expression of the stress-inducible gene group. When a plant is exposed to a stress, such as drought stress, signal-transduction occurs via ABA dependent pathway and ABA independent pathway, and the signal-transduction regulates the expression of the stress-inducible gene group. The gene group includes those involved in synthesis of compatible solutes, such as proline and glycine betaine. Proline and glycine betaine have been well studied. It is known that a transgenic plant, in which proline or glycine betaine is excessively accumulated by engineering the synthetic or decomposition system, shows resistance to NaCl or low temperature stress.

On the other hands in the biosynthetic pathway for RFO, galactinol is first synthesized by galactinol synthase. Next, raffinose is synthesized by raffinose synthase using galactinol and sucrose as substrates, and finally stachyose is synthesized by stachyose synthase using the raffinose and galactinol as substrates, as shown in FIG. 4. A generic name for raffinose and stachyose is RFO. So far, every report concerning RFO suggests that raffinose and stachyose plays an important role in drought resistance of seeds (Blackman S. A. et al. Plant Physiol. 100: 225–230, 1992, Ooms J. J. J. et al. Plant Physiol. 102: 1185–1192, 1993).

There is no report concerning functions or roles of RFO in a plant body other than those in a seed. A seed and a plant body may share an overlapping mechanism for acquiring drought resistance, or they may have totally different mechanisms.

For example, it is known that stresses, such as drought conditions, cause a plant to close stomata by accumulation of ABA as described above to suppress transpiration, thereby preventing water loss. Actually, ABA-deficient *Arabidopsis* mutants aba1 having an altered ABA synthetic system wither easily such that they cannot grow at a normal humidity. However, ABA-deficient mutant seeds can bud even under completely drought conditions. In other words, no decrease in drought resistance is found in ABA-deficient mutant seeds (Koornneef, M et al., Physiol. Plant. 61: 377–383, 1984, Duckham, S. C. et al., Plant Cell and Environ. 14: 601–606, 1991, Rock, C. D. and Zeevaart, J. A. D., Proc. Natl. Acad. Sci. 88: 7496–7499, 1991).

Moreover, seeds of ABA insusceptible *Arabidopsis* mutant abi3 are known to lack drought resistance. Under complete drought conditions, the seeds lose their budding ability. However, the seeds disseminated before progression of drying can bud, and no phenotype that withers like aba1 is observed (Nambara, E., et al, Polant J. 2: 435–441, 1992, Kriz, A. R., et al, Plant Physiol. 92: 538–542, 1990, Parcy, F., et al, Plant Cell 6: 1567–1582). In conclusion, ABI3 possesses a mechanism to acquire drought resistance, which functions only in its seed, and whose action is far greater than of ABA.

As described above, there is a great difference between a seed and a plant body in respect of drought resistance acquisition mechanism. Whether RFO, which is suggested to be important in drought resistance of a seed, plays a role in drought resistance of a plant body remains unknown and cannot even be predicted.

SUMMARY OF THE INVENTION

Accordingly, an object of the present invention is to provide a method for increasing stress resistance to a plant, which enables production of a plant having resistance against environmental stresses including drought and/or high salt concentration.

After thorough study, the inventors have completed the invention by finding that an increased content of raffinose in a plant body can provide the plant with stress resistance.

The present invention encompasses the followings:
(1) a method for increasing stress resistance to a plant wherein a raffinose synthase gene is introduced into the plant body.
(2) The method for increasing stress resistance to a plant according to (1) wherein the raffinose synthase gene is the following gene (a) or (b):
(a) a gene encoding a protein comprising an amino acid sequence represented by SEQ ID NO: 1,
(b) a gene encoding a protein comprising an amino acid sequence differing from the amino acid sequence of SEQ ID NO: 1 by deletion, substitution or addition of at least one or more amino acids, and having raffinose synthetic activity.
(3) The method for increasing stress resistance to a plant according to (1) wherein raffinose content in the plant body is increased.

(4) The method for increasing stress resistance to a plant according to (1) wherein raffinose synthetic activity in the plant body is improved.
(5) A method for increasing stress resistance to a plant which comprises increasing raffinose content in the plant body.
(6) A method for increasing stress resistance to a plant which comprises improving raffinose synthetic activity in the plant body.
(7) A method for increasing stress resistance to a plant which comprises excessively expressing the following (c) or (d) protein in the plant body:
(c) a gene encoding a protein comprising an amino acid sequence represented by SEQ ID NO: 1,
(d) a gene encoding a protein comprising an amino acid sequence differing from the amino acid sequence of SEQ ID NO: 1 by deletion, substitution or addition of at least one or more amino acids, and having raffinose synthetic activity.

DETAILED DESCRIPTION OF THE INVENTION

Figure 1:
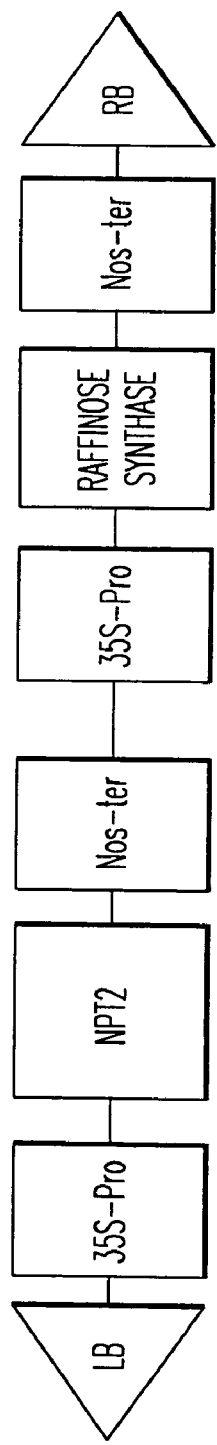
FIG. 1 is a schematic diagram of a vector plasmid for transformation having raffinose synthase gene derived from soybean.

More detailed description concerning the method for increasing stress resistance to a plant according to the present invention will be given as follows.

The method for increasing stress resistance to a plant according to this invention comprises the steps of introducing a gene (called raffinose synthase gene) that encodes raffinose synthase into a plant body so as to increase stress resistance to the plant. Examples of plants include, but are not limited to, *Arabidopsis, Glycine, Vicia,* rape-seed, *Helianthus, Gossypium,* sugar beat, *Oryza, Saccharum,* corn and *Sorghum.*

Any raffinose synthase gene may be used herein so far as it encodes a protein having raffinose synthase activity. Raffinose synthase activity is activity to synthesize raffinose using sucrose and galactinol as substrates. For example, a raffinose synthesis reaction is conducted by adding fractions, which contain raffinose synthase extracted from a plant body, to a reaction solution, which contains sucrose and galactinol. Then raffinose synthesized in the reaction solution is determined so that raffinose synthetic activity can be evaluated. After the expiration of a certain time, raffinose synthesis reaction can be ceased by adding ethanol in a volume 4 times the volume of the reaction solution, and heating at 95° C. for 30 seconds.

Raffinose synthase gene can also be prepared from a plant body. Any plant which synthesizes raffinose may be used. Such plants include *Arabidopsis, Vicia,* rape-seed, *Helianthus, Gossypium,* and sugar beat.

Nucleotide sequence information of the raffinose synthase gene can be obtained by searching genes having homology with raffinose synthase genes (SEQ ID NO: 2) derived from soybean based on a database, such as GenBank. Examples of homology analytical programs may include GENETIX-MAC (Gene information processing software, Software Development) which adopts the Lipman-Pearson method and programs available on the Internet. Nucleotide sequences thus obtained by the program as described above may or may not contain the full length gene. Even when the sequence does not contain the full length sequence, a full length sequence can be easily obtained by 5' RACE and 3' RACE using RNA extracted from a target plant tissue as a template and a primer corresponding to a site sharing high homology with a raffinose synthase gene derived from soybean. The resultant full length sequence is integrated into an appropriate expression vector, which is provided by a kit, such as Soluble Protein Expression system (INVITROGEN), Tight Control Expression System (INVITROGEN), or QIAexpress System (QIAGEN) for gene expression. Subsequently, raffinose synthase activity is measured as described above, and then clones having activity are screened. Detailed description for expressing genes are given in Plant Molecular Biology, A Laboratory Manual (Melody S. Clark (Ed.), Springer) and the like.

Moreover, a raffinose synthase gene can be obtained by preparing a cDNA library from poly(A)$^+$ RNA and by screening the cDNA library with hybridization. Probes used for hybridization can be obtained by PCR (Polymerase Chain Reaction, hereinafter referred to as PCR) amplification using oligonucleotides, which are synthesized based on a partial amino acid sequence of raffinose synthase, as primers.

Now, a method to obtain a raffinose synthase gene from poly(A)$^+$ RNA will be described in detail. Any site for extracting poly(A)$^+$ RNA may be used so far as a raffinose synthase gene expresses therefrom.

A method to extract total RNA is not limited, and any method which is effective in obtaining less-damaged RNA may be employed. Examples of such a method include the phenol/SDS method, guanidine isothiocyanate/cesium chloride method, and any known method. Then, poly(A)$^+$ RNA can be isolated from thus obtained total RNA using oligo (dT) carriers. In addition, any kit (MPG Direct mRNA Purification Kit, CPG, INC. and the like), by which poly(A)$^+$ RNA can be obtained without extracting total RNA, may be used.

To construct a cDNA library, first, a single-stranded cDNA is synthesized using poly(A)$^+$ RNA as a template and oligo(dT) primer, random primer and the like, and reverse transcriptase. Next, a double-stranded cDNA is synthesized by Gubler and Hoffman's method, Okayama-Berg method (Molecular Cloning 2$^{nd}$ edition, Cold Spring Harbor press, 1989) and the like. In case of a low expression amount of a raffinose synthase gene, cDNA may be amplified by PCR using a kit for constructing a cDNA library (Capfinder PCR cDNA Library Construction Kit (CLONTECH). Thus synthesized cDNA can be cloned into cloning vectors including phage vectors and plasmids by blunt-ending, addition of a linker, and addition of restriction enzyme sites by PCR.

DNA fragments used as probes for screening a cDNA library can be obtained by PCR. For example, a region containing highly conserved homology between plants, such as soybean and cucumber, is found based on the nucleotide sequence information of known raffinose synthase genes of the plants. This region can be used as a probe after amplification by PCR. In another example, a database containing genome nucleotide sequences of a plant for extraction is searched for a target gene homolog. Accordingly, a raffinose synthase gene homolog is identified in the plant for extraction so that a primer for PCR can be designed.

Probes for hybridization can be prepared by PCR using the primers designed and synthesized as described above and cDNA. In addition, a probe can also be prepared by the so-called RACE method (Rapid Amplification of cDNA End: PCR PROTOCOLS A Guide to Methods and Applications, ACADEMIC press INC. p.28–38). Examples of labels for probes include radioisotope, biotin, and other various substances. Preferably, labeling is performed by the random priming method. Further, screening is not only performed by hybridization, but also by PCR. Furthermore, a combination of hybridization and PCR may be employed.

Other than the above methods, the following methods can be used for cloning of a raffinose synthase gene.
(1) Raffinose synthase is isolated and purified from a plant body, and then a total nucleotide sequence is chemically synthesized based on the amino acid sequence determined.
(2) Chromosomal DNA is prepared from a plant body, chromosomal DNA library is constructed using plasmid vectors and the like. Then a raffinose synthase gene is obtained from the library by hybridization or PCR. Here, a raffinose synthase gene derived from a chromosome is predicted to have introns in the coding region. Even if DNA is divided by such introns, the DNA is included in the DNAs of this invention so far as it encodes raffinose synthase.
(3) Poly(A)$^+$RNA is fractioned by molecular weight and the like, and the fraction is subjected to in vitro translation system using wheat germ or rabbit blood reticulocytes. Then fractions, in which mRNA encoding a polypeptide having raffinose synthase activity, are determined, thereby constructing and obtaining a cDNA fragment of interest.
(4) A raffinose synthase antibody is prepared, and then cDNA library is integrated into a protein expression vector. Next, an appropriate host is infected with the vector to express the protein encoded by the cDNA. Using the antibody, cDNA of interest is screened.
(5) An appropriate primer is synthesized from an amino acid sequence of a peptide fragment, followed by amplification of a sequence containing the terminal by the RACE method. Then the amplified sequence is cloned.

For expression of a raffinose synthase gene, DNA of a region encoding the enzyme may be integrated into a variety of expression vectors. Detailed information on this matter is described in e.g., Plant Molecular Biology-A Laboratory Manual (M. S. Clark (eds.), Springer). Commercial expression vectors may be used herein. Expression can be confirmed by measuring activity according to the method described in this specification.

Examples of raffinose synthase genes include a gene encoding a protein comprising an amino acid sequence of SEQ ID NO: 1, or a gene encoding a protein comprising an amino acid sequence differing from that of SEQ ID NO: 1 by deletion, substitution, or addition of at least one or more amino acids and having raffinose synthetic activity. Moreover, an example of a raffinose synthase gene is a gene represented by SEQ ID NO: 2.

A raffinose synthase gene may be a gene encoding a raffinose synthase protein containing substitution, deletion, insertion, addition, or inversion of one or more amino acids at one or more positions so far as the protein have intact activity to synthesize raffinose from galactinol and sucrose. "Raffinose synthase activity" is activity to synthesize raffinose using sucrose and galactinol as substrates. That is, a fraction containing raffinose synthase extracted from a plant is added to a reaction solution having sucrose and galactinol to proceed raffinose synthetic reaction. Then raffinose synthetic activity can be evaluated by determining raffinose synthesized in the reaction solution. In addition, after expiration of a certain time, the raffinose synthetic reaction can be stopped by adding ethanol in a volume 4 times the volume of the reaction solution, and heating at 95° C. for 30 seconds. A protein considered to possess raffinose synthase activity should have activity of 30% or more, preferably 60% or more, more preferably 80% or more, most preferably 90% or more of that of raffinose synthase represented by SEQ ID NO: 1 or 2.

A method, known among persons in the art, for preparing a raffinose synthase gene encoding a protein consisting of an altered amino acid sequence is, for example in vitro mutagenesis by PCR (Tsuyoshi Izawa, in vitro mutagenesis by PCR, pp 151–158, ed., Isao Shimamoto, Takuji Sasaki, Cell Engineering, special number, Plant Cell Engineering Series 7, New PCR Experimental Protocol, Shu-jun sha). Number of the amino acid for artificial alteration is 200 or less, preferably 100 or less, more preferably, 50 or less, more preferably 10 or less. In nature, mutation in a nucleotide sequence may cause mutation in an amino acid sequence of a protein. Such a mutated raffinose synthase gene encoding a protein consisting of an amino acid sequence differing from that of a natural type raffinose synthase gene by substitution, deletion, addition, and/or insertion of one or more amino acids may also be included in the raffinose synthase gene of this invention, so far as it encodes a protein having raffinose synthetic activity. Moreover, mutation in a nucleotide sequence may not cause mutation in an amino acid in a protein (degenerate mutation). Such a degenerate mutant is also included in the raffinose synthase gene of this invention.

Such a raffinose synthase gene encoding a protein consisting of an amino acid sequence other than that of SEQ ID NO: 1 can be obtained. For example, a nucleotide sequence of raffinose synthase gene represented by SEQ ID NO: 2 is altered by site-specific mutagenesis so that the amino acid at a specific site is substituted, deleted, inserted, or added. Furthermore, an altered raffinose synthase gene as described above can also be obtained by known standard techniques for mutation. Example of such techniques include a method, in which raffinose synthase gene is treated in vitro with e.g., hydroxylamine, and a method, in which bacteria involved in the genus *Escherichia* retaining raffinose synthase genes are treated under UV irradiation, or with mutagens, normally used for artificial mutation, including N-methyl-N'-nitro-N-nitrosoguanidine (NTG) or nitrous acid.

Further, substitution, deletion, insertion, addition or inversion of bases as described above includes naturally occurring mutations based on plant body individual differences, inbred difference, multiplication of a gene, differences among each of organs and tissues.

A raffinose synthase gene encoding raffinose synthase which has an amino acid sequence other than that of SEQ ID NO: 1 can be obtained by expression of a raffinose synthase gene having mutation as described above, followed by examination of raffinose synthetic activity in expression products. Furthermore, a raffinose synthase gene encoding raffinose synthase and having an amino acid sequence other than that of SEQ ID NO: 1 can be obtained by isolating DNA which hybridizes to a raffinose synthase gene containing a mutation under stringent conditions and encodes a protein having raffinose synthase activity. The term "stringent conditions" indicates a condition in which so-called specific hybrids are formed and nonspecific hybrids are not formed. It is difficult to convert precisely the stringent conditions into numeric values. For example, a condition which allows hybridization of DNAs having homology of 50% or more to each other, but allows no hybridization of DNAs having homology of less than 50%. Another example is a condition which allows hybridization at a salt concentration corresponding to normal washing conditions for Southern hybridization, which consists of 60° C., 1×SSC and 0.1%SDS, preferably, 0.1×SSC and 0.1% SDS. Genes capable of hybridizing under such conditions include those containing a stop codon inserted or losing activity due to a mutated active center. However, such a gene can be easily removed by integrating it to a commercial expression vector and measuring raffinose synthase activity by the method as described above. A protein, which is considered to possess raffinose synthase activity, should have activity of 30% or more, preferably 60% or more, more preferably 80% or more, most preferably 90% or more of that of raffinose synthase represented by SEQ ID NO: 1 or 2.

A transgenic plant, which excessively expresses raffinose synthetease, can be obtained by introducing raffinose synthase gene as described above into the plant body. To introduce a raffinose synthase gene, an expression vector, to which the raffinose synthase gene is integrated downstream of a certain promoter, is constructed. When an expression vector is constructed, the methods described in e.g., Plant Molecular Biology—A Laboratory Manual (M. S. Clark (eds.), Springer) are employed appropriately. Commercial vectors may be used. Methods of transformation are not specifically limited. Examples of transformation methods include a method for infecting with Agrobacteria (see Japanese Patent Laid Open Publication No. 2-58917), electroporation (see Japanese Patent Laid Open Publication No. 5-68575), the particle gun method (see Japanese Patent Laid Open Publication No. 5-508316). Particularly, transformation for plants belonging to the family Brassicaceae can be performed according to the method described in Plant Cell Reports (1987), 6, 321–325. Transformation for soybeans can be performed according to the methods described in Pro. Natl. Acad. Sci. USA, 86. 145 (1989), TIBTECH, 8, 145 (1990), Bio/Technology, 6, 923 (1988), Plant Physiol., 87, 671 (1988), Plant Physiol., 91, 1212 (1992), Bio/Technology, 6, 915 (1988), Plant Physiol., 99, 81 (1992) and the like. Transformation for rice can be performed according to the method described in Experimental Protocol for Model Plant, Rice and *Arabidopsis thaliana* (p. 78). Expression of a raffinose synthase gene can be confirmed by measuring activity by the method as described in this specification.

The resulting transgenic plant possesses improved stress resistance. The term "stress" indicates, for example high salt concentration and/or drought condition. The transgenic plant can suppress the amount of water absorbed by soil by suppressing the transpiration rate. Here the term "drought condition" indicates a condition under which wild type plants can grow, but growth is suppressed because of limited humidity and water supply. Further, the term "high salt concentration" is not specifically limited, but indicates a condition in which the salt content of agricultural fertilizers, acidic soil, or alkaline soil (e.g., NaCl) is high.

Improved resistance against stress including high salt concentration and/or drought conditions means that the degree of growth suppression is subdued even under conditions which suppress the growth or allow no growth of wild type plants. Examples of growth evaluation methods include, but are not limited, growth rate, plant length, weight, leaf area, flower fertility, pollen fertility, seed weight or yield, or a combination of these.

Transgenic plants may be homozygotes, or heteroprogeny plants obtained by back crossing a wild type plant with a homozygote. Moreover, stress resistance of a heterozygote may be more improved than that of a wild type plant, and stress resistance of a homozygote may be more improved than that of a heterozygote.

Raffinose content in a plant body can be increased by introducing a raffinose synthase gene into the plant body. Raffinose is one of raffinose family oligosaccharides, in which galactose is connected to glucosyl group of sucrose via α-1,6 linkage. Raffinose is synthesized by raffinose synthase using galactinol and sucrose as substrates. When raffinose content in a plant body is measured, first, fluid containing raffinose is extracted from a plant body. The extract can be obtained from a plant body as follows. That is, the extract is frozen with liquid nitrogen, crushed, added with 10 ml of 80% ethanol preheated to 80° C., and then boiled for 10 minutes at 90° C. Then this series of steps is repeated twice (a total of three rounds of these steps is performed).

Next, the extract is determined with HPLC (high-speed liquid chromatography). HPLC can be performed using sugar analysis system DX500 (CarboPac MA1, pulsed amperometry detector (Dionex Corporation). As described above, determination of raffinose content in an extract from a plant enables detection of an increase in raffinose content in the plant.

In this method, "increased raffinose content" indicates that a plant body to be measured contains raffinose in an amount greater than that in a wild type plant body grown under the same conditions as the transgenic plant. More specifically, it indicates that raffinose content per rosette leaf (fresh weight) is 1.1 to 50 fold, preferably 2 to 30 fold, more preferably 5 to 20 fold greater than that of an intact wild type plant. More preferably, it indicates that raffinose content (fresh weight) of a whole plant body is 1.1 to 50 fold, preferably 2 to 30 fold, more preferably 5 to 20 fold greater than that of an intact wild type plant body.

Raffinose content of a plant body can also be increased by improving raffinose synthetic activity in the plant body so as to increase stress resistance to the plant. Raffinose synthetic activity is activity to synthesize raffinose using sucrose and galactinol as substrates. For example, a fraction containing raffinose synthase extracted from a plant body is added to a reaction solution having sucrose and galactinol to proceed raffinose synthetic reaction. Then raffinose synthetic activity can be evaluated by determining raffinose synthesized in the reaction solution. In addition, after the expiration of a certain time, the raffinose synthetic reaction can be stopped by adding ethanol in a volume 4 times the volume of the reaction solution, and heating at 95° C. for 30 seconds.

Moreover, "increased raffinose synthetic activity in a plant body" means that activity or specific activity per fresh weight or per leaf of a transgenic plant body is improved compared to raffinose synthase activity of a wild type plant grown under the same conditions. More specifically it indicates that activity per fresh weight of a rosette leaf is 1.1 to 50 fold, preferably 2 to 30 fold, more preferably 5 to 20 fold greater than that of an intact wild type plant body. More preferably, it indicates that activity per fresh weight of a whole plant body is 1.1 to 50 fold, preferably 2 to 30 fold, more preferably 5 to 20 fold greater than that of an intact wild type plant body. However, intrinsic raffinose synthase activity in a wild type plant body cannot always be detected depending on species or habitat. In this case, "improved raffinose synthetic activity of a plant body" indicates that the plant body possesses activity to a detectable degree.

Examples of a method to increase raffinose synthetic activity in a plant body include a method, in which a raffinose synthase gene is incorporated into a vector that allows gene expression, and the vector is introduced into a plant; a method, in which a raffinose synthase gene is introduced onto a plant chromosome; a method, in which a gene encoding galactinol synthase that is upstream enzyme of raffinose synthase and a raffinose synthase gene are incorporated into a vector that allows gene expression, and the vector is introduced into a plant; a method, in which a gene encoding a galactinol synthase that is upstream enzyme of a raffinose synthase and a raffinose synthase gene are introduced onto a chromosome of a plant; and a method, in which a gene encoding a transcriptional factor that enhances expression of a raffinose synthase gene on a chromosome is introduced into a plant.

Alternatively, screening may be performed for a mutant showing improved expression of a raffinose synthase gene. For example, in a method to increase raffinose synthetic activity using a chemical mutagenesis agent, such as ethylmethane sulfonate (EMS), a protein is extracted from mutants obtained using a chemical mutagenesis agent, such as ethylmethane sulfonate (EMS), followed by screening by Western blot analysis or ELISA for those having large protein mass of raffinose synthase.

All publications, patents and patent applications, particularly International publication No. WO98/49273, cited herein are incorporated into this specification by reference in their entirety.

EXAMPLE

Now a more detailed description of the present invention will be provided using examples. The technical scope of this invention is not limited by the following examples.

Example 1

1. Construction of a Vector Plasmid for Transformation

A raffinose synthase gene used herein was derived from soybean as described in International Publication No. WO98/49273. A plasmid for transformation was constructed using a plasmid pBI121 (CLONTECH) derived from pBIN19, as shown in FIG. 1. That is, GUS gene of pBI121 located between a cauliflower mosaic virus 35S promoter (denoted as "35S-Pro" in FIG. 1) and a nopalin synthase gene terminator (denoted as "Nos-ter" in FIG. 1) was substituted by a raffinose synthase cDNA derived from soybean (denoted as "Raffinose Synthase" in FIG. 1).

More specifically, a XbaI-SacI fragment was obtained by PCR using a primer, containing a XbaI site added upstream of an initiation codon at the 156$^{th}$ base; and a primer, containing a SacI site at the 1260$^{th}$ base in the nucleotide sequence of SEQ ID NO: 2 having a gene encoding raffinose synthase derived from soybean. Further, a region from the SacI site at the 1260$^{th}$ base to the termination codon at the 2448$^{th}$ base, to which SacI site had been added, was amplified. The vector pBI121 was digested with XbaI and SacI to remove GUS gene, followed by ligation with XbaI-SacI and SacI-SacI fragments amplified using soybean raffinose synthase cDNA as a template. The ligation mix was transformed into *E.coli* HB101, and then the plasmid sequence was analyzed. Thus, a plasmid having a soybean raffinose synthase cDNA sequence was selected and designated as pBI121-sSRS.

2. Transformation

The vector plasmid (pBI121-sSRS) prepared in 1 above was introduced into *Agrobacterium tumefaciens* C58 by the triparental mating method, thereby preparing *Agrobacterium tumefaciens* C58/pBI121-sSRS. The obtained *Agrobacterium tumefaciens* C58/pBI121-sSRS was transformed into *Arabidopsis thariana* col-0 (LEHLE SEEDS) by the vacuum infiltration method.

The resultant seeds were sterilized and sowed over a selection medium containing 25 μg/ml kanamycin to allow selection of transformants. Seedlings exhibiting resistance to kanamycin were planted in rock fiber containing 1000× HYPO Nex solution and grown under 12 hours of light at 22° C. for acclimation. In addition, transformation of *Arabidopsis* plant and selection of drug-resistant plants were performed according to the method described in "Experimental Protocol for Model Plant; *Oryza sativa* and *Arabidopsis thaliana*" (ed., Isao Shimamoto and Kiyotaka Okada, Shu-jun sha).

For the 5 lines of transformants (referred to as SRS-1 to 4) that were obtained, introduction of the genes was confirmed by PCR using the following primers 1 and 2, and genome DNA.

Primer 1: 5'-TTT CCG GTT CAA GTTATG GT-3' (SEQ ID NO: 3)

Primer 2: 5'-CAATGCATC CGT TAT CAG TA-3' (SEQ ID NO: 4)

Genome DNA to be used as a template was purified using Plant DNeasy DNA extraction kit (QIAGEN) from a leaf of T2 generation of candidate transformants which had been selected based on drug-resistance. Following 97° C. for 1 min. of beat denaturation process, PCR was performed 30 cycles, each of which consisting of 95° C. for 15 sec., 56° C. for 15 sec. and 72° C. for 60 sec. Following PCR, amplified DNA fragments were confirmed by agarose gel electrophoresis.

3. Analysis of Expression of Introduced Genes in Transformant Plant

Expression of raffinose synthase gene derived from soybean was confirmed in transformant plants SRS-1 to 5 by Northern hybridization and Western blot analysis. Moreover, raffinose synthase activity in the transformant plants was examined.

<Northern Hybridization Analysis>

Figure 2:
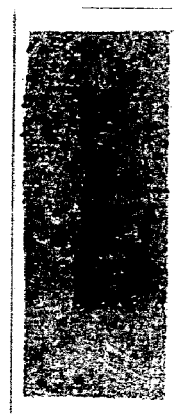
FIG. 2 is a photograph of electrophoresis showing the results of Northern blot analysis for expression of raffinose synthase gene derived from soybean.

Total RNA was extracted and purified from leaves of a T3 generation plant. RNA was extracted using Rneasy Plant Mini Kit (QIAGEN). Twenty μg each of the extracted RNA was subjected to electrophoresis using denaturation gel, and transferred to HybondN$^+$. PCR was performed using pBI121-sSRS as a template and the above primers 1 and 2, thereby obtaining DNA fragments. The amplified DNA fragments were labeled with AlphosDirect (Amersham Pharmacia Biotech) and used as probes. Hybridization of the probe to HybondN$^+$ was performed at 60° C. overnight, and then washed with a buffer preheated to 60° C. according to the protocol of the kit. FIG. 2 shows the result of detecting the probes hybridized to HybondN$^+$ using CDP-Star (Pharmacia Biotech). In FIG. 2, lane 1 denotes wild type, lane 2 denotes SRS-1, lane 3 denotes SRS-2, lane 4 denotes SRS-3, and lane 5 denotes SRS-4.

<Western Blot Analysis>

First, raffinose synthase derived from soybean was expressed in *E.coli* in order to prepare an antibody to raffinose synthase derived from soybean.

A plasmid for expression of raffinose synthase derived from soybean in *E.coli* was constructed as follows. Raffinose synthase cDNA derived from soybean was cloned into Nde1 and BamH1 sites of a pET16b vector Next, a fragment containing Nde1 site that had been added to ATG (initiation codon from $156^{th}$ to $158^{th}$ bases) and XhoI site from $579^{th}$ to $581^{st}$ bases was amplified by PCR. The amplified fragment and XhoI-BamHI fragment of SRS cDNA were cloned together into NdeI and BamHI sites of pET16b (NOVAGEN). Subsequently, a BamHI-BamHI fragment containing a termination codon immediately followed by a BamHI site was amplified by PCR. The amplified fragment was cloned into a BamHI site of pET16b having SRSNdeI-BamHI fragment connected thereto. The nucleotide sequence of the plasmid constructed was analyzed, and then a clone having the correct nucleotide sequence of raffinose synthase derived from soybean was selected. The resulting plasmid was designated as pET16bSRS. The plasmid pET16bSRS was transformed into E.coli BL21(DE3)pLysS (Stratagene) and the transformants (E.coli) were stored at −80° C.

E.coli BL21(DE31)pLys/pET16bSRS was pre-cultured overnight in a LB medium containing 50 μg/ml carbenicillin. The culture solution 0.1 ml was inoculated in 50 ml of a medium, cultured for approximately 3 hours, added with 1 mM (final concentration) IPTG, followed by another 3 hours of culturing. The culture solution was centrifuged at 8000 rpm for 20 minutes, thereby collecting bacteria. The collected bacteria were treated using B-PER kit (PIERCE), thereby obtaining soluble and insoluble fractions. As a result of confirmation of expression of raffinose synthase derived from soybean by SDS-PAGE, raffinose synthase derived from soybean was present in insoluble fractions.

The insoluble fraction was dissolved in 8 M urea, and then raffinose synthase derived from soybean-HisTag fusion protein was purified using a His-Ttrap column (Pharmacia Biotech). The fusion protein was used to immunize a rabbit, thereby obtaining an antibody to raffinose synthase derived from soybean.

Western blot analysis was conducted using the thus obtained antibody to raffinose synthase derived from soybean. First, a plant to be analyzed was homogenized under liquid nitrogen with a mortar, followed by extraction with an extraction buffer (50 mM Tris-HCl, 5 mM DTT, 1 mM PMSF, 0.1% PolyclarAT, pH 7.0). The extract was filtered through Miracloth (Calbiochem), and the filtrate was centrifuged with cooling. Next, the centrifuged supernatant was applied on PD-10 column (Pharmacia Biotech) to remove low molecular substances, and then concentrated in Centriprep 10 (amicon) to obtain crude extract. The crude extract was subjected to SDS-PAGE.

Multi gel 7.5% (Daiichi-Kayaku) was used for SDS PAGE. Following electrophoresis, the extract was electroblotted onto PVDF membrane (BIORAD). Western blot analysis was conducted using amplified AP immuneblot kit (BIORAD). A band of raffinose synthase derived from Arabidopsis was detected for Arabidopsis thaliana Col-0; a band of raffinose synthase derived from soybean was detected for soybean immature seeds; and both bands were detected for the transformants (SRS-1 to 4).

<Examination of Raffinose Synthetic Activity in a Transformant Plant>

Using the crude extract as obtained in the above Western blot analysis, raffinose synthetic activity in transformant plants was examined. Raffinose synthetic activity was determined by adding the crude extract to the enzyme reaction solution having a composition as follows. The reaction solution was prepared to final concentration with the following composition. Ten to 50 μl of the rough extract was added to the reaction solution to a total volume of 100 μl, allowing raffinose synthetic reaction to proceed at 32° C. for 60 to 120 minutes.

Reaction Solution Composition
2.5 mM sucrose (Nacalai Tesque)
5.0 mM galactinol (Wako Pure Chemical Industries, Ltd.)
5.0 mM DTT (nacalai tesque)
20.0 mM Tris hydrochloric acid (pH 7.0) (nacalai tesque)

After the expiration of a certain time, ethanol in a volume 4 times the volume of the reaction solution was added to the reaction solution. The mixture was heated at 95° C. for 30 seconds to stop the raffinose synthetic reaction. Next, the reaction solution was centrifuged, and then the centrifuged supernatant was dried up under reduced pressure. Then, the product was dissolved in distilled water, and raffinose in the reaction solution was determined by sugar analysis system. The sugar analysis system employed herein was DX500 (Dionex Corporation), the column was CarboPac PA1 (4×250) (Dionex Corporation), and the detector was PAD (Dionex Corporation). Table 1 shows the results.

TABLE 1

|  | Raffinose (nmol/hr/mg) protein |
|---|---|
| Col-o | — |
| s-SRS-1 | 14.0 |
| s-SRS-2 | 4.7 |
| s-SRS-3 | 6.7 |
| s-SRS-4 | 7.2 |

— not detected

4. Drought Resistance of Transformant Plant

Drought resistance of Arabidopsis plants expressing raffinose synthase derived from soybean described in 3 above was evaluated.

The transformant plant seeds obtained in 3 above and wild type seeds were sterilized, sown on GM agar medium plate having the following composition, and then grown under 12 hours of light at 22° C.

GM Agar Medium Composition (pH 5.7 (KOH))
1L Murashige-Skoog salt medium (Sigma)
1 ml×1000 B5 vitamin solution (Sigma)
0.5 g MES (nacalai tesque)
30 g of sucrose (nacalai tesque)
8 g of agar BA30 for medium (Ina Shokuhin Kogyo-sha)

A GM agar medium plate was prepared by mixing the above components, sterilizing with an autoclave, and dispensing the mixture into a Petri dish with a diameter of 9 cm.

Three weeks after germination on the GM agar medium plate, the plant bodies were planted in a vinyl pot with a diameter of 8 cm and a height of 6 cm (T0–8) containing Metromix 350 wetted with 1000×HYPO Nex. Seven plants were planted per pot. The pot was put into a vat, wrapped with Saran wrap (Asahi Chemical Industry Co., Ltd.) to avoid drying for 3 days, and then the Saran wrap was removed. To the vat, 1000×HYPO Nex was added to the height of 1 cm. Whenever the water level decreased, water was added to maintain the level.

Figure 3:
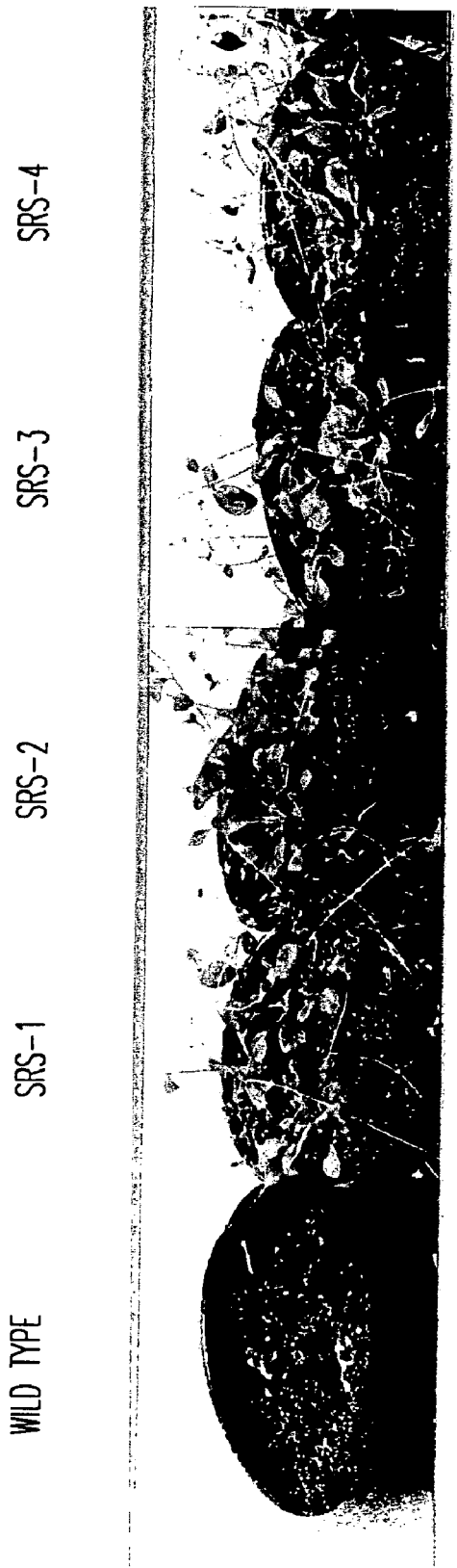
FIG. 3 is a photograph showing the growth of transformant plants under drought conditions.
Figure 4:
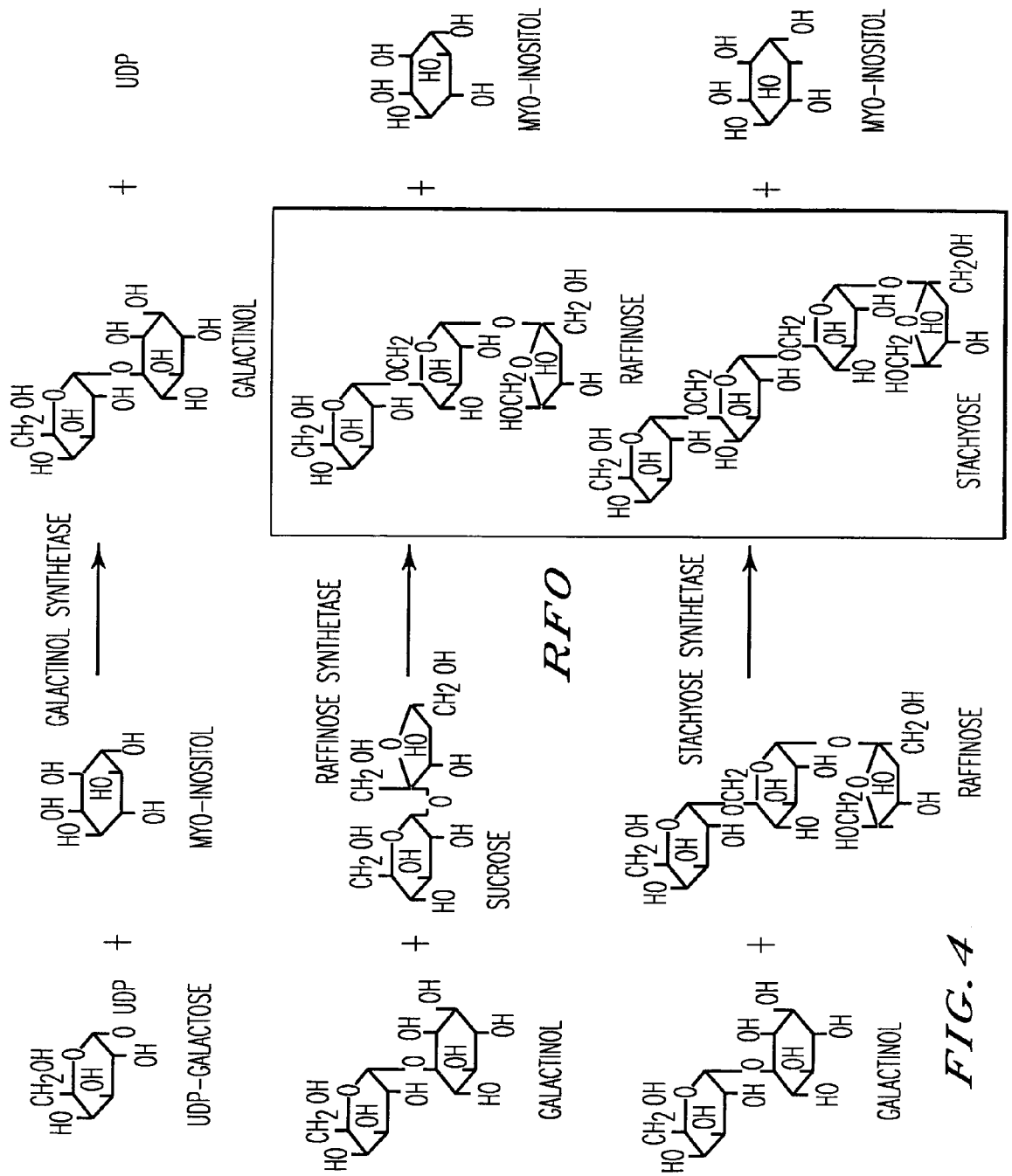
FIG. 4 is a schematic diagram showing the RF0 synthetic pathway.

One week after transplantation, the pot was placed on a kim towel for 30 minutes, removing water in the pot as far as possible. Then, the pot was subjected to drying treatment in a dry vat. FIG. 3 shows the plants 3 weeks after drying treatment. As shown in FIG. 3, the transformants exhibited drought resistance superior to wild type plants. In conclusion, expression of a large mount of raffinose in a plant body can increase good drought resistance to the plant.

As described in detail above, according to the present invention, expression of a large amount of raffinose in a plant body can increase stress resistance to the plant. That is, a plant having resistance to various kinds of environmental stresses can be generated according to the present invention.

Sequence Listing Free Text

SEQ ID NOS: 3 and 4 are synthetic primers.

What is claimed is:

1. A method of increasing the drought resistance of plants, comprising
introducing a polynucleotide encoding a protein having raffinose synthase activity into plants, and
selecting transformed plants having raffinose synthetic activity of at least 4.7 nmol/hr/mg.

2. The method of claim 1, wherein the plant is selected from the group consisting of *Arabidopsis, Glycine, Vicia*, rape-seed, *Helianthus, Gossypium*, sugar beet, *Oryza, Saccharum*, corn, and *Sorghum*.

3. The method of claim 1, wherein the polynucleotide is introduced into the plant on a vector.

4. The method of claim 1, wherein the polynucleotide is introduced into a chromosome of the plant.

5. The method of claim 1, wherein the protein comprises the amino acid sequence in SEQ ID NO: 1.

6. A method of increasing the drought resistance of plants, comprising:
introducing a polynucleotide encoding a protein having raffinose synthase activity into plants, wherein said polynucleotide comprises SEQ ID NO: 2 or a polynucleotide that hybridizes under stringent conditions to SEQ ID NO: 2, wherein the stringent conditions comprise washing at 60° C. in 1×SSC and 0.1% SDS, and
selecting transformed plants having raffinose synthetic activity of at least 4.7 nmol/hr/mg.

7. The method of claim 6, wherein the plant is selected from the group consisting of *Arabidopsis, Glycine, Vicia*, rape-seed, *Helianthus, Gossypium*, sugar beet, *Oryza, Saccharum*, corn, and *Sorghum*.

8. The method of claim 6, wherein the polynucleotide is introduced into the plant on a vector.

9. The method of claim 6, wherein the polynucleotide is introduced into a chromosome of the plant.

10. The method of claim 6, wherein the polynucleotide comprises SEQ ID NO: 2.

11. A method of increasing resistance to high salt concentration in plants,
comprising introducing a polynucleotide encoding a protein having raffinose synthase activity into plants, and
selecting transformed plants having raffinose synthetic activity of at least 4.7 nmol/hr/mg.

12. The method of claim 11, wherein the plant is selected from the group consisting of *Arabidopsis, Glycine, Vicia*, rape-seed, *Helianthus, Gossypium*, sugar beet, *Oryza, Saccharum*, corn, and *Sorghum*.

13. The method of claim 11, wherein the polynucleotide is introduced into the plant on a vector.

14. The method of claim 11, wherein the polynucleotide is introduced into a chromosome of the plant.

15. The method of claim 11, wherein the protein comprises the amino acid sequence in SEQ ID NO: 1.

16. A method of increasing resistance to high salt concentration in plants, comprising:

introducing a polynucleotide encoding a protein having raffinose synthase activity into plants, wherein said polynucleotide comprises SEQ ID NO:2 or a polynucleotide that hybridizes under stringent conditions to SEQ ID NO:2, wherein the stringent conditions comprise washing at 60° C. in 1×SSC and 0.1% SDS, and selecting transformed plants having raffinose synthetic activity of at least 4.7 nmol/hr/mg.

17. The method of claim 16, wherein the plant is selected from the group consisting of *Arabidopsis, Glycine, Vicia*, rape-seed, *Helianthus, Gossypium*, sugar beet, *Oryza, Saccharum*, corn, and *Sorghum*.

18. The method of claim 16, wherein the polynucleotide is introduced into the plant on a vector.

19. The method of claim 16, wherein the polynucleotide is introduced into a chromosome of the plant.

20. The method of claim 16, wherein the polynucleotide comprises SEQ ID NO:2.

* * * * *